United States Patent [19]

Forman et al.

[11] Patent Number: 4,501,966
[45] Date of Patent: Feb. 26, 1985

[54] INFRARED MICROSCOPE INSPECTION APPARATUS

[75] Inventors: Steven E. Forman, Framingham; James W. Caunt, Concord, both of Mass.

[73] Assignee: Massachusetts Institute of Technology, Cambridge, Mass.

[21] Appl. No.: 243,415

[22] Filed: Mar. 13, 1981

[51] Int. Cl.³ .............................................. H01J 31/50
[52] U.S. Cl. .................................................. 250/332
[58] Field of Search ................................ 250/332, 341

[56] References Cited

U.S. PATENT DOCUMENTS 4,337,395  6/1982  Alexander et al. ................. 250/332

Primary Examiner—Davis L. Willis
Attorney, Agent, or Firm—Arthur A. Smith, Jr.; Paul J. Cook

[57] ABSTRACT

Apparatus and system for inspecting infrared transparents, such as an array of photovoltaic modules containing silicon solar cells, includes an infrared microscope, at least three sources of infrared light placed around and having their axes intersect the center of the object field and means for sending the reflected light through the microscope. The apparatus is adapted to be mounted on an X-Y translator positioned adjacent the object surface.

6 Claims, 4 Drawing Figures

INFRARED MICROSCOPE INSPECTION APPARATUS

The Government has rights in this invention pursuant to Contract No. DE-ACOR-76ET20279 awarded by the Department of Energy.

BACKGROUND OF THE INVENTION

This invention relates to an apparatus and system for inspecting a surface transparent to infrared radiation for defects. More particularly, this invention relates to a portable apparatus and system for inspecting such surfaces.

The need for data regarding the performance and long term reliability of a photovoltaic solar array has created the need for inspection equipment to aid in this task. Flat plate (non-concentrating) photovoltaic arrays currently consist of commercially manufactured panels with electrical strings of silicon wafers, gallium arsenide surfaces or the like, wired in a series-parallel arrangement and either encapsulated or mounted under some type of protective cover plate.

Typical damage to this type of array under normal, long-term operating conditions might consist of: fractured solder joints, encapsulant delamination, cracked cells or split interconnects. All above noted defects can be characterized as mechanical or macro-defects and can, under laboratory conditions, be located using conventional microscope techniques. Of these defects, cracked silicon cells are most prevalent, difficult to identify and the most time dependent. A crack in the silicon wafer which crosses a surface conductor can electrically open a series string in a module and stop the flow of current through that string.

Several useful semiconductor materials including silicon, which are opaque in visible light, are transparent to near-infrared radiation. The transmission of silicon cuts-on sharply between 0.9-1.1 microns and extends out to beyond 2.5 microns before significant drop-off. Infrared microscopy makes possible the observation of the internal structure of silicon semiconductor devices, including evaluation of the substrate and lead attachments on the back side of the wafer. This technique is routinely used by manufacturers of semiconductor devices.

This technique has utility in locating cracks in relatively large silicon solar cells. Observation of cracks at visible wavelengths is limited to only that portion of the crack lying in the surface plane of the wafer. In the absence of significant surface displacements of the cell adjacent to the crack, the visual information needed to locate and identify a crack is severely limited. Resolution losses through an optical system further reduce the possibility of defect identification.

The number of panels and cells that make up a large field installation along with the physical size of the array render currently available inspection techniques unsatisfactory. One must tolerate long inspection times, operator discomfort and difficulty in reaching all parts of the array surface, in order to achieve a statistically representative sample of inspection data. Accordingly, such an inspection device must address these problems, should be portable and should be universally adaptable to the currently used array frame mechanical configurations.

SUMMARY OF THE INVENTION

In accordance with this invention, an inspection apparatus is provided which includes an infrared microscope, at least three sources of infrared radiation placed around and having their axes intersect the center of the object field and means for sensing the reflected infrared radiation through the microscope. The microscope, sources of infrared radiation and the radiation sensing means are adapted to be mounted on an X-Y translator positioned over the object surface so that the inspection apparatus can be moved over the entire object surface. The system and apparatus of this invention are portable and can be utilized in places where access is difficult. The axis of the microscope is positioned orthogonal to the surface being inspected. The infrared radiation sources are positioned at an angle to the microscope axes of between about 15° and 60°, preferably, between about 30° and 40°, more preferably 35°, in order to maximize the formation of shadows of defects or other features not orthogonal to the optical axis. It is necessary to utilize at least three, preferably at least five, sources of infrared radiation in order to receive reflected or scattered radiation from cracks which are at any angle on the cell. The lights preferably are positioned equidistant from each other in order to uniformly illuminate the test surface.

DESCRIPTION OF SPECIFIC EMBODIMENTS

Figure 1:
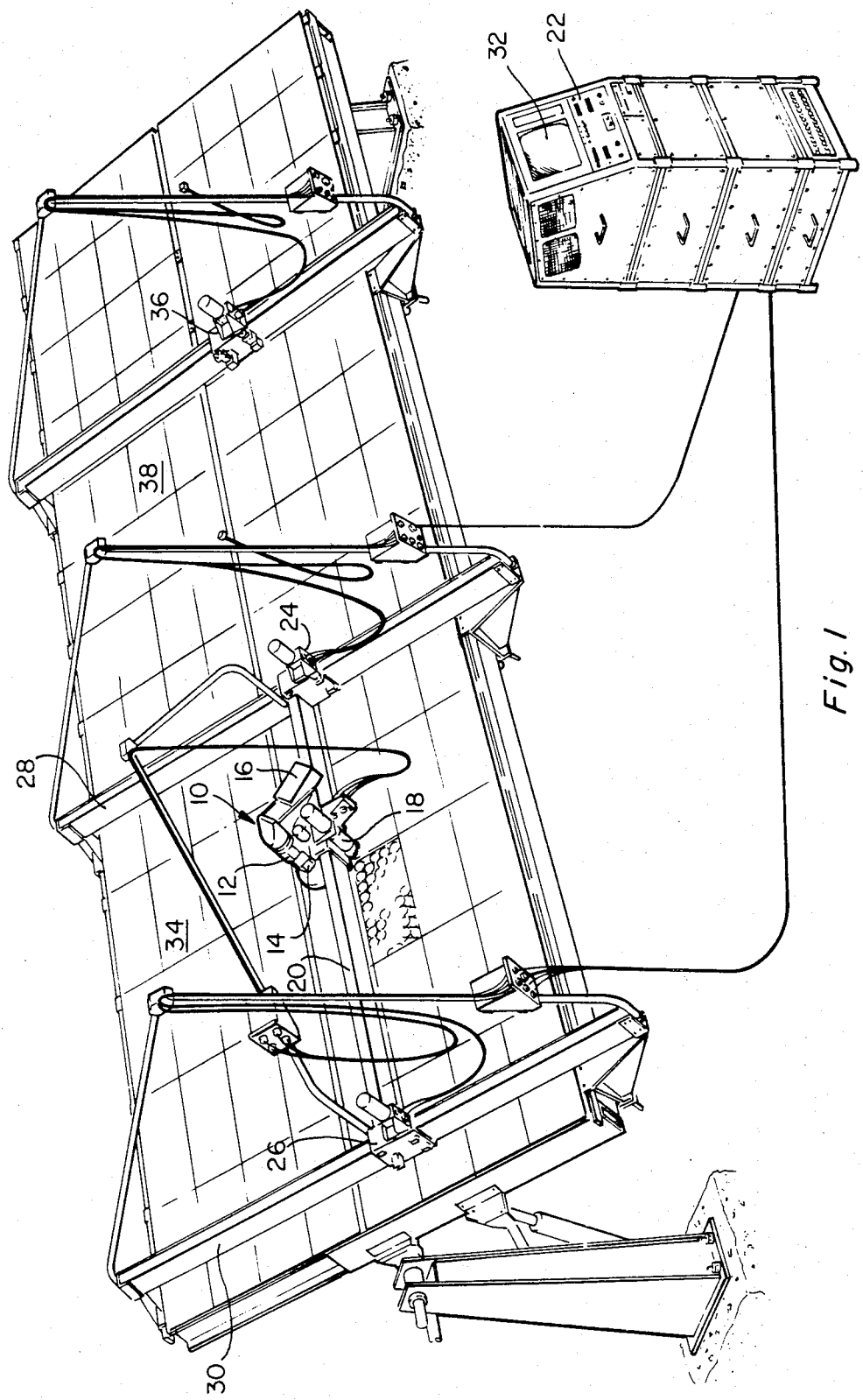
FIG. 1 is a perspective view of the system of this invention.

Referring to FIG. 1, the system of this invention includes the test apparatus 10 which includes a microscope 12, a plurality of infrared radiation sources 14 and an infrared to visible conversion tube 16. The test apparatus 10 is mounted on a motorized conveyor 18 that traverses bar 20 in response to a signal from control console 22. Bar 20 is mounted on motorized conveyors 24 and 26 which are adapted to traverse bars 20 and 30 respectively in response to a signal from control console 22. An image from infrared sensor 16 can be transmitted to the screen 32 mounted on console 22. The combination of the bars 20, 28 and 30 and the motorized conveyors 18, 24 and 26 permit viewing of the entire solar collector surface 34. After the solar surface 34 has been monitored, the bar 20 and motorized conveyor 18 can be detached from motorized conveyors 24 and 26 and can be then positioned between motorized conveyors 24 and 36 in order to permit monitoring surface area 38.

Figure 2:
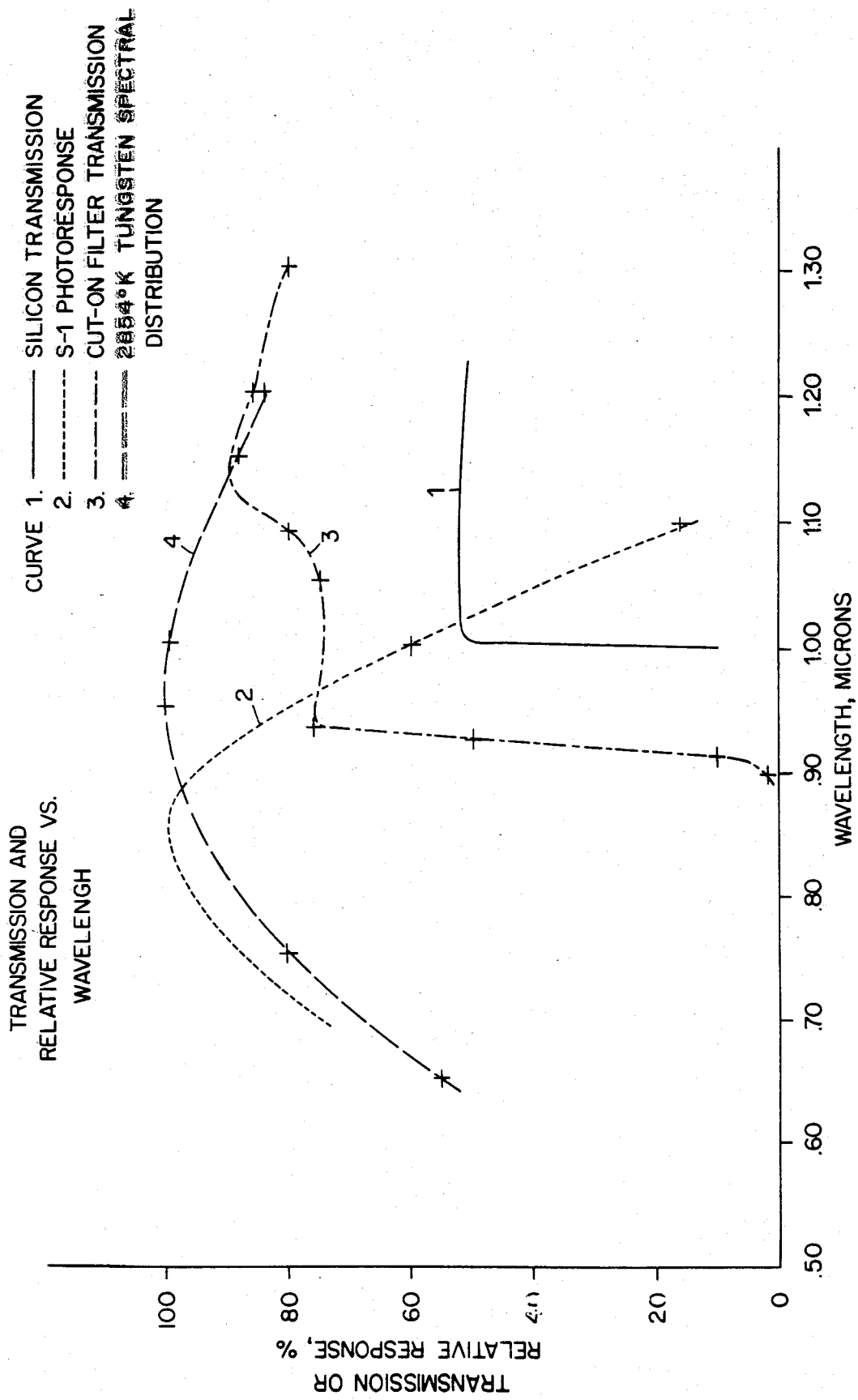
FIG. 2 is a graph of the relative response and transmission versus light wavelength of typical test material and components of the system of this invention.

Referring to FIG. 2, the transmission and relative response of silicon such as is utilized in silicon solar cells is shown in curve. The transmission of a cut-on filter positioned between a visible plus infrared light source of this invention and the object surface area is shown by curve 3. The relationship between relative response and wavelength for tungsten having a temperature of 2854° K. is shown by curve 4 and the further response of the infrared image converter shown by curve 2.

Figure 3:
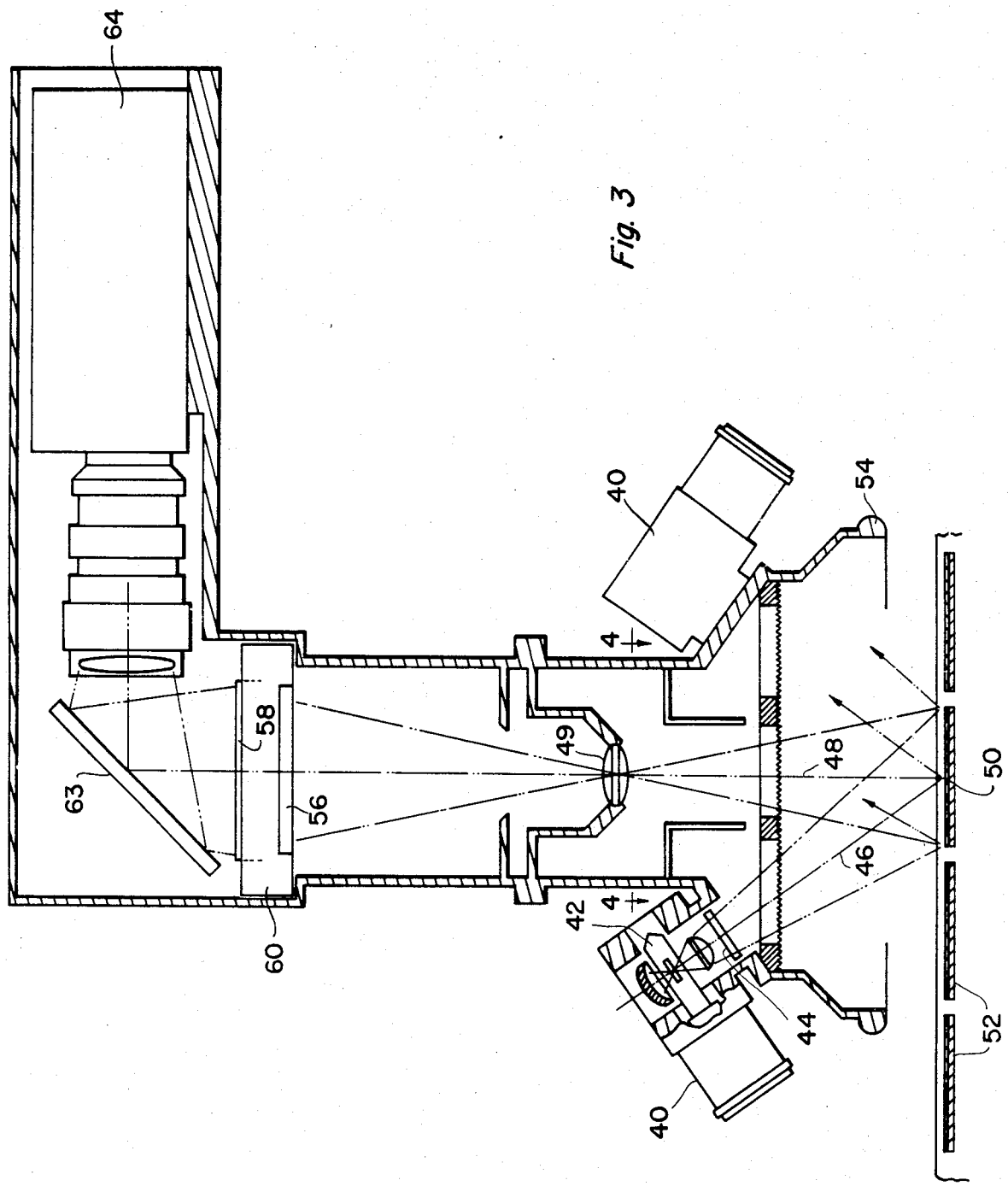
FIG. 3 is a vertical cross sectional view of the apparatus of this invention.
Figure 4:
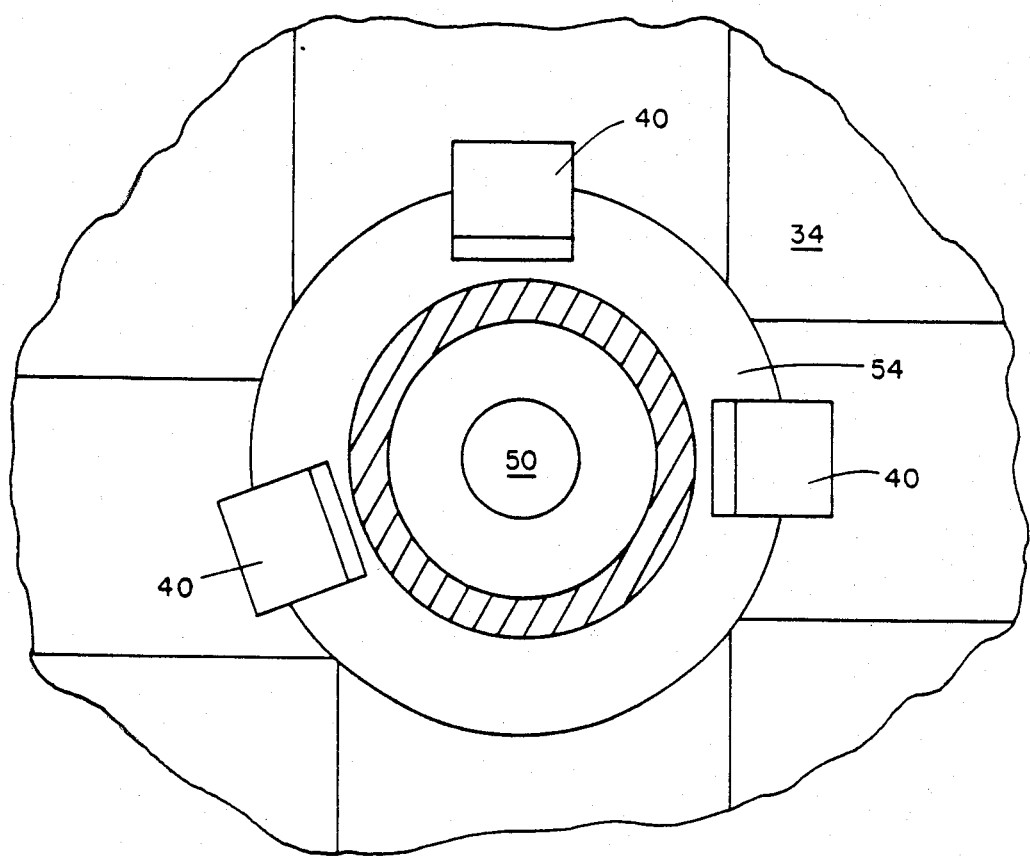
FIG. 4 is a cross sectional view of the apparatus of FIG. 3 taken along line 4—4.

Referring to FIGS. 3 and 4, the test apparatus of this invention includes a plurality of infrared radiation sources 40, each of which includes a quartz-halogen lamp 42 and cut-on filter 44 having the characteristics typically shown by curve 3 of FIG. 2. The axis 46 of the infrared source 40 is positioned to coincide with the central axis 48 of the microscope objective 49 at the covering surface or outer surface 50 of the silicon solar cell 52. The test apparatus includes a sun shroud and baffle 54. The reflected infrared radiation passes through microscope objective 49 to irradiate the photocathode 56 of the infrared image converter tube. The infrared image converter tube 60 produces a visible image of the object cell, which appears on the red phosphor output screen 58. The visible image is reflected from mirror 62 into camera 64 for transmittal to screen 32 on console 22.

The following example illustrates the present invention and is not intended to limit the same.

EXAMPLE I

A typical system showing the elements which make up the infrared microscope and its accompanying camera and monitor is shown in FIG. 3. The microscope objective 49 having a 1.25X magnification forms an image of the entire cell on the photocathode 56 of the image converter tube 60. A proximity focused diode image tube with a 75 mm field, S-1 photo-response (see FIG. 2, curve 2), and a red phosphor output, was chosen. The large photocathode 56 provides a maximum spatial resolution (50-1-P/mm) in relation to the field size. As can be seen in FIG. 2, the S-1 photo-response provides sufficient overlap of wavelengths between approximately 1 to 2 microns, in order to maximize the useful integrated radiant power. The red phosphor output screen is spectrally matched to the inherent peak red sensitivity of the LLTV silicon diode array camera. The proximity-focused diode tube was chosen because of its simplicity of design and relatively low gain requirements. The overall radiant power gain (Gw) of the image tube=0.8 watts/watt. This tube is available from the Electro-Optical Products Division of ITT Corporation.

FIGS. 3 and 4 show an arrangement of three dark-field infrared radiation sources, placed in a conical plane around and having their axes coincident with the center of the object field, as shown. When using 5 of these sources each consisting of a 100 watt quartz-tungsten halogen miniature lamp, condensers and a cut-on filter having the transmission properties shown in FIG. 2, curve 3, can be utilized. FIG. 2, curve 4, shows the output of the quartz-tungsten-halogen lamp relative to wavelength, peaking near 1.0 microns. As can be seen from the curve, filter transmission exceeds 80 percent at 1.1 microns. Each radiation source can be individually cooled with a miniature blower, chosen to minimize rotor inertia and resulting loss of resolution from instrument vibration. The useable radiant power output of each source equals approximately 10 watts.

In dark-field illumination, a large portion of the incident radiation is reflected off the object 34 and out of the field of view of the microscope objective. With perfectly specular reflection, the object field 34 would appear completely dark. However, radiation which is reflected, scattered or forms shadows of defects or other features not orthogonal to the optical axis, will be imaged by the objective. This approach was chosen to maximize relative brightness of the cell defects (primarily cracks), as compared to the radiation reflected from the surface of the cell. In practice, reflections from the cell conductors do considerable scattering and appear quite bright in the image field. With this system, laboratory observations have shown penetration of 1.0 micron radiation in silicon to depths greater than 1 mm. This penetration allows imaging of the full height of a crack in the silicon wafer, thereby maximizing the obtained visual information, which is necessary, as will be shown, to overcome the inherent resolution loss contributed by the video system.

The output of the image tube red phosphor screen 58 is spectrally matched to the peak red sensitivity of the video camera silicon diode array. The phosphor screen illumination is equal to approximately 20 lumens/ft$^2$, which is well within low light sensitivity of the silicon diode array camera tube.

The video monitor 32, which is located in the control console 22, is equipped with a 14" screen having a resolution of 800 lines. The line width resolution of the video monitor largely determines the limit of the overall system resolution, and is equal to approximately 0.003" on the object. This will limit the smallest detectable defect only when it does not cross a line scan. The loss of resolution contributed by the image tube (0.001" over entire surface) results in an overall system resolution of approximately 0.004" or 10 lines/mm.

The theoretical depth of focus at 1 micron is approximately 0.010", while the actual depth of focus over which there is no noticeable image blur, is approximately 0.030". This will require periodic adjustment of the focus to image defects at various heights in the silicon wafer, and also to accommodate mechanical height variations of the solar panels. The instrument has a remote focus control at the console.

The overall system magnification is the ratio of the monitor screen size divided by the size of the field being imaged, and can be adjusted manually within the range of 5X to 15X. Optimum magnification is determined by balancing defect size against inspection time to cover a given array area.

The remote-controlled translator moves the test device 10 in X and Y typically over an 8'×8' array area, usually equal to 1 cell spacing. Coordinates of the instrument field are read-out on the console, and recorded as part of the inspection data. Both photographic and video tape recording of the display output at the console can be utilized.

This complete device can be manually moved from one 8'×8' array area to the next for complete inspection of large, operating photovoltaic arrays. In addition, the X-Y translator mounting brackets can be easily modified to interface with a variety frame styles, thereby accommodating many array installations.

We claim:

1. Apparatus for illuminating an infrared transparent surface with infrared light and measuring light reflected through said surface which comprises:
    a. means for irradiating said surface with infrared radiation from at least three sources, each of said sources being positioned at an angle between about 15° and 60° from the orthogonal direction to said surface,
    b. a lens positioned above said surface having its axis orthogonal to said surface and adapted to receive infrared radiation reflected from said surface,
    c. means for converting infrared radiation transmitted through said lens to visible light, and d. means for sensing said visible light.

2. The apparatus of claim 1 wherein said angle is between about 30° and 40°.

3. The apparatus of claim 1 wherein said sensing means comprises a television camera.

4. A system for irradiating an infrared transparent surface with infrared radiation and transmitting an image of said surface, comprising the apparatus of claim 1 mounted on means for moving said apparatus in both the X and Y directions over an extended surface area formed from said infrared transparent surface.

5. A system for irradiating an infrared transparent surface with infrared radiation and transmitting an image of said surface, comprising the apparatus of claim 2 mounted on means for moving said apparatus in both the X and Y directions over an extended surface area formed from said infrared transparent surface.

6. A system for irradiating an infrared transparent surface with infrared radiation and transmitting an image of said surface comprising the apparatus of claim 3 mounted on means for moving said apparatus in both the X and Y directions over an extended surface area formed from said infrared transparent surface.

* * * * *